US011555764B1

(12) United States Patent
Srikrishna

(10) Patent No.: US 11,555,764 B1
(45) Date of Patent: Jan. 17, 2023

(54) DYNAMIC MODIFICATION OF BIOAEROSOL DETECTION WITH GENETIC IDENTIFICATION

(71) Applicant: Patient Knowhow, Inc., San Mateo, CA (US)

(72) Inventor: Devabhaktuni Srikrishna, San Francisco, CA (US)

(73) Assignee: Patient Knowhow, Inc., San Mateo, CA (US)

( * ) Notice: Subject to any disclaimer, the term of this patent is extended or adjusted under 35 U.S.C. 154(b) by 269 days.

(21) Appl. No.: 17/101,311

(22) Filed: Nov. 23, 2020

Related U.S. Application Data

(60) Provisional application No. 62/972,387, filed on Feb. 10, 2020, provisional application No. 62/948,710, filed on Dec. 16, 2019, provisional application No. 62/939,791, filed on Nov. 25, 2019.

(51) Int. Cl.
*G01N 1/22* (2006.01)
*G01N 33/497* (2006.01)
*C12Q 1/6869* (2018.01)
*G01N 15/06* (2006.01)

(52) U.S. Cl.
CPC ......... *G01N 1/2202* (2013.01); *C12Q 1/6869* (2013.01); *G01N 15/06* (2013.01); *G01N 33/497* (2013.01); *G01N 2001/2223* (2013.01); *G01N 2015/0693* (2013.01); *G01N 2033/4975* (2013.01); *G01N 2333/01* (2013.01); *G01N 2333/08* (2013.01)

(58) Field of Classification Search
CPC ............ G01N 1/2202; G01N 15/0656; G01N 33/497; G01N 2001/2223; G01N 2033/4975; G01N 2333/01; G01N 2333/08; C12Q 1/6869
See application file for complete search history.

(56) References Cited

U.S. PATENT DOCUMENTS 10,359,748 B2   7/2019   Elbsat et al.
2006/0257853 A1*  11/2006  Herman ................ G08B 21/12
435/5

OTHER PUBLICATIONS

A. Kumar et al., "Evolution of Selective-Sequencing Approaches For Virus Discovery and Virome Analysis," Virus Res. 239, pp. 172-179, Jul. 15, 2017, doi:10.1016/j.virusres.2017.06.005.

(Continued)

*Primary Examiner* — Benjamin R Schmitt
(74) *Attorney, Agent, or Firm* — Huse IP Law; Charles C. Huse

(57) ABSTRACT

A bioaerosol detector is operated in accordance with one or more first inputs. Operating the bioaerosol detector includes filtering pathogens from the air, extracting genetic material from the filtered pathogens, and analyzing the extracted genetic material to identify the filtered pathogens. While operating the bioaerosol detector in accordance with the one or more first inputs, a change is identified in an operating condition for the bioaerosol detector. In response, the bioaerosol detector is operated in accordance with one or more second inputs. At least one input of the one or more second inputs is distinct from a respective input of the one or more first inputs.

23 Claims, 9 Drawing Sheets

(56) References Cited

OTHER PUBLICATIONS

A. Petrackova et al., "Standardization of Sequencing Coverage Depth in NGS: Recommendation for Detection of Clonal and Subclonal Mutations in Cancer Diagnostics," Frontiers in Oncology, vol. 9, Article 851, Sep. 4, 2019, doi: 10.3389/fonc.2019.00851.

A.A. Ayginin et al., "The Study of Viral RNA Diversity in Bird Samples Using De Novo Designed Multiplex Genus-Specific Primer Panels," vol. 2018, 10 pp., Aug. 12, 2018, https://doi.org/10.1155/2018/3248285.

A.J. Prussin II et al., "Seasonal dynamics of DNA and RNA viral bioaerosol communities in a daycare center," Microbiome 7:53, 2019, https://doi.org/10.1186/s40168-019-0672-z.

A.L. Greninger et al., "Rapid metagenomic identification of viral pathogens in clinical samples by real-time nanopore sequencing analysis," Genome Medicine 7:99, 13 pp., 2015, DOI 10.1186/s13073-015-0220-9.

B. Huang et al., "Illumina sequencing of clinical samples for virus detection in a public health laboratory," Nature Scientific Reports, 9:5409, Apr. 1, 2019, https://doi.org/10.1038/s41598-019-41830-w.

B.E. Draper et al., "Real-Time Analysis and Signal Optimization for Charge Detection Mass Spectrometry," Journal of the American Society for Mass Spectrometry, vol. 30, pp. 898-904, Apr. 16, 2019.

B.M. O'Flaherty et al., "Comprehensive viral enrichment enables sensitive respiratory virus genomic identification and analysis by next generation sequencing," Genome Research 28, pp. 869-877, 2018.

C. Coles et al., "The Acute Respiratory Infection Consortium: A Multi-Site, Multi-Disciplinary Clinical Research Network in the Department of Defense," Military Medicine, vol. 184, S2, pp. 44-50, Nov./Dec. 2019, doi: 10.1093/milmed/usz174.

C. Gaines, "Army scientists brief peers on biodefense," 20th CBRNE Command, Jul. 13, 2018, https://www.dvidshub.net/news/printable/284173.

C. Rinke et al., "Validation of picogram- and femtogram-input DNA libraries for microscale metagenomics," PeerJ 4: e2486, Sep. 22, 2016, DOI 10.7717/peerj.2486.

C.A. Corzo et al., "Airborne Detection and Quantification of Swine Influenza A Virus in Air Samples Collected Inside, Outside and Downwind from Swine Barns," PLOS ONE 8:8, Aug. 8, 2013, doi:10.1371/journal.pone.0071444.

C.B. Matranga et al., "Enhanced methods for unbiased deep sequencing of Lassa and Ebola RNA viruses from clinical and biological samples," Genome Biology 15:519, 2014, doi:10.1186/s13059-014-0519-7.

C.F. Fronczek et al., "Biosensors for Monitoring Airborne Pathogens," Journal of Laboratory Automation 20:4, pp. 390-410, 2015.

C.F. Manso et al., "Efficient and unbiased metagenomic recovery of RNA virus genomes from human plasma samples," Nature Scientific Reports 7:4173, Jun. 23, 2017, DOI:10.1038/s41598-017-02239-5.

C.M. Malboeuf et al., "Complete viral RNA genome sequencing of ultra-low copy samples by sequence-independent amplification," Nucleic Acids Research 41:1, p. e13, Sep. 8, 2012, doi:10.1093/nar/gks794.

D. Lewandowska et al., "Optimization and validation of sample preparation for metagenomic sequencing of viruses in clinical samples," Microbiome 5:94, 2017, DOI 10.1186/s40168-017-0317-z.

D. Verreault et al., "Methods for Sampling of Airborne Viruses," Microbiology and Molecular Biology Reviews 72:3, pp. 413-444, Sep. 2008, doi:10.1128/MMBR.00002-08.

E.S. Bailey et al., "Molecular surveillance of respiratory viruses with bioaerosol sampling in an airport," Tropical Diseases, Travel Medicine and Vaccines 4:11, 2018, https://doi.org/10.1186/s40794-018-0071-7.

F. Cobo, "Application of MALDI-TOF Mass Spectrometry in Clinical Virology: A Review," The Open Virology Journal, 7, pp. 84-90, 2013.

G.H. Wan et al., "Detection of Common Respiratory Viruses and Mycoplasma pneumoniae in Patient-Occupied Rooms in Pediatric Wards," Medicine 95:14, p. e3014, Apr. 2016, DOI: 10.1097/MD.0000000000003014.

Global Preparedness Monitoring Board, "A World at Risk: Annual report on global preparedness for health emergencies," World Health Organization, 2019, https://apps.who.int/gpmb/assets/annual_report/GPMB_annualreport_2019.pdf.

H. Branswell, "CDC made a synthetic Ebola virus to test treatments. It worked," STAT, Jul. 9, 2019.

I.E. Agranovski et al., "Miniature PCR based portable bioaerosol monitor development," Journal of Applied Microbiology 122, pp. 129-138, 2016.

Illumina, "An introduction to Next-Generation Sequencing Technology," 2017.

Illumina, "Culture-Free Detection and Identification of Unknown RNA Viruses," Application Note: Sequencing, 2014.

J. Quick et al., "Multiplex PCR method for MinION and Illumina sequencing of Zika and other virus genomes directly from clinical samples," Nature Protocols, 12:6, May 24, 2017, doi:10.1038/nprot.2017.066.

J. Yan et al., "Infectious virus in exhaled breath of symptomatic seasonal influenza cases from a college community," PNAS, 115:5, pp. 1081-1086, Jan. 30, 2018, www.pnas.org/cgi/doi/10.1073/pnas.1716561115.

J.J. Thomas et al., "Electrospray ion mobility spectrometry of intact viruses," Spectroscopy 18, pp. 31-36, 2004.

J.K. Lewis et al., "Identification of viral mutants by mass spectrometry," Proc. Natl. Acad. Sci. USA 95, pp. 8596-8601, Jul. 1998.

J.L. Sanchez et al., "Respiratory Infections in the U.S. Military: Recent Experience and Control," Clinical Microbiology Reviews 28:3, Jul. 17, 2015, doi:10.1128/CMR.00039-14.

K. Lewandowski et al., "Metagenomic Nanopore sequencing of influenza virus direct from clinical respiratory samples," Journal of Clinical Microbiology 58:1, Dec. 23, 2019, DOI: 10.1128/JCM.00963-19.

K. Rosario et al., "Diversity of DNA and RNA Viruses in Indoor Air as Assessed via Metagenomic Sequencing," Environmental Science & Technology 52, pp. 1014-1027, 2018, DOI: 10.1021/acs.est.7b04203.

K.K. Coleman et al., "Bioaerosol Sampling for Respiratory Viruses in Singapore's Mass Rapid Transit Network," Nature Scientific Reports, 8:17476, 2018, Nov. 30, 2018, DOI:10.1038/s41598-018-35896-1.

K.M. Wylie et al., "Detection of Viruses in Clinical Samples by Use of Metagenomic Sequencing and Targeted Sequence Capture," Journal of Clinical Microbiology 56:12, p. e01123-18, Sep. 19, 2018, https://doi.org/10.1128/JCM.01123-18.

L. Ladhani et al., "Sampling and detection of airborne influenza virus towards point-of-care applications," PLoS ONE, 12:3, p. e0174314, Mar. 28, 2017, https://doi.org/10.1371/journal.pone.0174314.

L.E. Kafetzopoulou et al., "Assessment of metagenomic Nanopore and Illumina sequencing for recovering whole genome sequences of chikungunya and dengue viruses directly from clinical samples," Euro Surveill. 23:50, Dec. 13, 2018, https://doi.org/10.2807/1560-7917.ES.2018.23.50.1800228.

L.F. Pease III, "Physical analysis of virus particles using electrospray differential mobility analysis," Trends in Biotechnology 30:4, Apr. 2012, doi:10.1016/j.tibtech.2011.11.004.

M.H. Hjelmso et al., "Metagenomic analysis of viruses in toilet waste from long distance flights—A new procedure for global infectious disease surveillance," PLoS ONE, 14:1, p. e0210368, Jan. 14, 2019, https://doi.org/10.1371/journal.pone.0210368.

M.I.L. Sjoholm et al., "Multiplex Detection of Human Herpesviruses from Archival Specimens by Using Matrix-Assisted Laser Desorption Ionization—Time of Flight Mass Spectrometry," Journal of Clinical Microbiology 46:2, pp. 540-545, Feb. 2008, doi:10.1128/JCM.01565-07.

N. Ngaosuwankul et al., "Influenza A viral loads in respiratory samples collected from patients infected with pandemic H1N1, seasonal H1N1 and H3N2 viruses," Virology Journal 7:75, 2010, doi: 10.1186/1743-422X-7-75.

(56) References Cited

OTHER PUBLICATIONS

N. Peel et al., "Semi-quantitative characterisation of mixed pollen samples using MinION sequencing and Reverse Metagenomics (RevMet)," Methods in Ecology and Evolution 2019:00, pp. 1-12, DOI: 10.1111/2041-210X.13265.

N. Singhal et al., "MALDI-TOF mass spectrometry: an emerging technology for microbial identification and diagnosis," Frontiers in Microbiology, 6:791, Aug. 5, 2015, doi:10.3389/fmicb.2015.00791.

N.A. Be et al., "Metagenomic Analysis of the Airborne Environment in Urban Spaces," Environmental Microbiology 69:346-355, Oct. 29, 2014, DOI 10.1007/00248-014-0517-z.

National Academies of Sciences, Engineering, and Medicine, Biodefense in the Age of Synthetic Biology, Washington, DC: The National Academies Press, 2018, https://doi.org/10.17226/24890.

P. Fabian et al., "Airborne influenza virus detection with four aerosol samplers using molecular and infectivity assays: considerations for a new infectious virus aerosol sampler," Indoor Air 19:5, pp. 433-441, Oct. 2009, doi:10.1111/i.1600-0668.2009.00609.x.

R. Cumeras et al., "Review on Ion Mobility Spectrometry. Part 1: Current Instrumentation," Analyst 140:5, pp. 1376-1390, Mar. 7, 2015, doi:10.1039/c4an01100g.

R. Sampath et al., "Comprehensive Biothreat Cluster Identification by PCR/Electrospray-Ionization Mass Spectrometry," PLoS ONE 7:6, p. e36528, Jun. 29, 2012, doi: 10.1371/journal.pone.0036528.

R.J. Hall et al., "Evaluation of rapid and simple techniques for the enrichment of viruses prior to metagenomic virus discovery," Journal of Virological Methods vol. 195, pp. 194-204, 2014.

R.J. Hall et al., "Metagenomic Detection of Viruses in Aerosol Samples from Workers in Animal Slaughterhouses," PLoS ONE 8:8, p. e72226, Aug. 14, 2013, doi:10.1371/journal.pone.0072226.

R.S. Dhillon et al., "The Fight Against Zika Can't Wait for a Vaccine," Harvard Business Review, Aug. 18, 2016, https://hbr.org/2016/08/the-fight-against-zika-cant-wait-for-a-vaccine.

R.S. Noyce et al., "Construction of an infectious horsepox virus vaccine from chemically synthesized DNA fragments," PLoS ONE 13:1, p. e0188453, Jan. 19, 2018, https://doi.org/10.1371/journal.pone.0188453.

S.A. Solonenko, "Sequencing platform and library preparation choices impact viral metagenomes," BMC Genomics 14:320, 2013, doi:10.1186/1471-2164-14-320.

S.A. Trauger et al., "Investigating Viral Proteins and Intact Viruses with Mass Spectrometry," Top Curr Chem 225, pp. 265-282, 2003, DOI 10.1007/b10476.

S.M. Goyal et al., "Detection of viruses in used ventilation filters from two large public buildings," American Journal of Infection Control 39:7, pp. e30-38, Sep. 2011, doi:10.1016/j.ajic.2010.10.036.

Stefano Colombo et al., "Characterization of airborne viromes in cheese production plants," Journal of Applied Microbiology 125:5, pp. 1444-1454, Jul. 12, 2018, https://doi.org/10.1111/jam.14046.

T. Reed, "Nanopore Sequencing for Biosurveillance in South Korea," 20th CBRNE Command, Jun. 11, 2019.

T. Sugai, "Mass and Charge Measurements on Heavy Ions," Mass Spectrometry 6(3): S0074, 2017, DOI: 10.5702/massspectrometry.S0074.

T. Wongsurawat et al., "Rapid Sequencing of Multiple RNA Viruses in Their Native Form," Frontiers in Microbiology 10:260, Feb. 25, 2019, doi: 10.3389/fmicb.2019.00260.

T.M. Korves et al., "Detection of respiratory viruses on air filters from aircraft," Letters in Applied Microbiology 53, pp. 306-312, 2011.

T.W. Whon et al., "Metagenomic Characterization of Airborne Viral DNA Diversity in the Near-Surface Atmosphere," Journal of Virology 86:15, pp. 8221-8231, May 23, 2012, doi:10.1128/JVI.00293-12.

V. Neira et al., "Characterization of Viral Load, Viability and Persistence of Influenza A Virus in Air and on Surfaces of Swine Production Facilities," PLoS ONE 11:1, p. e0146616, Jan. 12, 2016, doi:10.1371/journal.pone.0146616.

V.N. Bui et al., "Bioaerosol Sampling to Detect Avian Influenza Virus in Hanoi's Largest Live Poultry Market," Clinical Infectious Diseases 2019:68, pp. 972-975, Aug. 31, 2018.

W.A. Kleefsman, Aerosol MALDI Mass Spectrometry for Bioaerosol Analysis, Delft University of Technology, 2008.

W.E. Bischoff et al., "Detection of Measles Virus RNA in Air and Surface Specimens in a Hospital Setting," The Journal of Infectious Diseases 2016:213, pp. 600-603, Sep. 19, 2015.

Y. Li et al., "VIP: an integrated pipeline for metagenomics of virus identification and discovery," Nature Scientific Reports, 6:23774, Mar. 30, 2016, DOI: 10.1038/srep23774.

Y.P. Ho et al., "Identification of Pathogens by Mass Spectrometry," Clinical Chemistry 56:4, pp. 525-536, 2010, DOI: 10.1373/clinchem.2009.138867.

* cited by examiner

300 ⤵

```
┌─────────────────────────────────────────────────────────────────────────┐
│ Operate a bioaerosol detector in accordance with one or more first inputs: filter pathogens (e.g., │
│ viruses and/or bacteria) from the air, extract genetic material from the filtered pathogens, and │
│ analyze the extracted genetic material to identify the filtered pathogens. (302) │
│                                                                          │
│  ┌ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┐   │
│    Perform genetic sequencing of extracted genetic material to identify filtered pathogens. (304) │
│  └ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┘   │
│  ┌ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┐   │
│    Perform spectrometry for extracted genetic material to identify filtered pathogens. (306) │
│  └ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┘   │
│  ┌ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┐   │
│    Use a microarray to analyze extracted genetic material to identify filtered pathogens. (308) │
│  └ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┘   │
│  ┌ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┐   │
│    The one or more inputs include detection time, filtering rate, genetic-sequencing rate, false- │
│    positive detection rate, and/or false-negative detection rate. (310) │
│  └ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┘   │
└─────────────────────────────────────────────────────────────────────────┘
                                    │
                                    ▼
                         ╱ Identify a change in an ╲     312-No
                        ╱     operating condition?   ╲ ──────────▶
                        ╲          312              ╱
                         ╲                         ╱
                                    │
                                 312-Yes
                                    ▼
┌─────────────────────────────────────────────────────────────────────────┐
│ Operate the bioaerosol detector in accordance with one or more second inputs. At least one input of the │
│ one or more second inputs is distinct from a respective input of the one or more first inputs. (314) │
└─────────────────────────────────────────────────────────────────────────┘
```

```
┌─────────────────────────────────────────────────────────────────────────────┐
│ Generate a cost function defining a cost of operating a bioaerosol detector as a function of biological │
│                   load setpoints for the genetic sequencer(s). (402)                    │
└─────────────────────────────────────────────────────────────────────────────┘
                                        │
                                        ▼
┌─────────────────────────────────────────────────────────────────────────────┐
│ Modify the cost function to account for an initial purchase cost and/or a benefit of a new asset. (404) │
└─────────────────────────────────────────────────────────────────────────────┘
                                        │
                                        ▼
┌─────────────────────────────────────────────────────────────────────────────┐
│ Use the modified cost function to determine values for decision variables including the biological load │
│                                setpoints. (406)                             │
├─────────────────────────────────────────────────────────────────────────────┤
│   Perform an optimization using the modified cost function to determine optimal values for the    │
│                            decision variables. (408)                        │
└─────────────────────────────────────────────────────────────────────────────┘
                                        │
                                        ▼
┌─────────────────────────────────────────────────────────────────────────────┐
│ Use the decision variables including the biological load setpoints to operate the genetic sequencer(s). │
│                                   (410)                                     │
└─────────────────────────────────────────────────────────────────────────────┘
```

Figure 4

DYNAMIC MODIFICATION OF BIOAEROSOL DETECTION WITH GENETIC IDENTIFICATION

RELATED APPLICATIONS

This application claims priority to U.S. Provisional Patent Application Nos. 62/939,791, filed Nov. 25, 2019, titled "Sequencing Cost Optimization of Bioaerosol Detection"; 62/948,710, filed Dec. 16, 2019, titled "Dynamic Modification of Bioaerosol Detection with Genetic Identification"; and 62/972,387, filed Feb. 10, 2020, titled "Dynamic Modification of Bioaerosol Detection with Genetic Identification, " which applications are hereby incorporated by reference in their entirety.

TECHNICAL FIELD

This disclosure relates to bioaerosol detectors for detecting viruses or bacteria in the air, and more specifically to dynamically modifying operation of such bioaerosol detectors.

BACKGROUND

Respiratory pathogens such as viruses and bacteria present a significant risk to public health. This risk is demonstrated by outbreaks such as the 1918 influenza pandemic, the 2016 Zika outbreak, and repeated Ebola outbreaks. The World Health Organization, in its September 2019 report "The World at Risk," warned that respiratory pathogens, such as an especially deadly strain of influenza or a disease-causing microorganism engineered or recreated in a laboratory, could spread across the world within three days, eventually killing an estimated 50-80 million people. No vaccine or treatment for a novel pathogen, whether natural or synthetic, can be approved and manufactured in three days. Furthermore, a pathogen such as the Zika virus could asymptomatically infect an entire population before being detected.

Synthetic biology, which allows viruses and other pathogens to be recreated or modified in a laboratory, presents a serious risk of misuse. In 2018, the horsepox virus, an extinct virus related to smallpox, was recreated and instructions for recreating it were published. In 2019, the Centers for Disease Control and Prevention (CDC) recreated the Ebola virus for drug testing. A different state actor or non-state actor might recreate or strengthen a pathogen with less noble intentions.

Viral detection is especially challenging. Each cubic meter of air can contain 1,000 to 100,000 (i.e., $10^3$ to $10^5$) contagious viruses near infected people or animals. The density of viruses in the air depends on the distance to an infected source. Sneezes and coughs by the infected source can increase the viral concentration further. The ability to scan for such viruses is desirable so that areas in which the contagion is present can be identified and avoided or quarantined. Since preventing infection is delay-sensitive, the speed of detection is an important variable. The collection of viruses in the air is RNA/DNA limited, however, so detection will not always be instantaneous. For example, detection may take tens of minutes if not hours. Furthermore, there are an estimated $10^6$ to $10^7$ viruses of all types per cubic meter in the near-surface atmosphere. With only $10^3$ to $10^5$ infectious viruses per cubic meter, signal to noise will be a fundamental tradeoff for detecting infectious viruses. And unlike bacteria, novel or emerging viruses with gene sequences that not been observed before have no conserved genomic signature: there is no localized portion of a virus's genome that can be targeted for identification without prior knowledge of the viral gene sequence. Identifying novel viruses with targeted techniques (e.g. PCR, which uses primers that are already present in the detector at the time of detection) is therefore challenging.

SUMMARY

According, there is a need for bioaerosol detectors that can efficiently and effectively identify respiratory pathogens.

In some embodiments, a method of bioaerosol detection includes operating a bioaerosol detector in accordance with one or more first inputs. Operating the bioaerosol detector includes filtering pathogens from the air, extracting genetic material from the filtered pathogens, and analyzing the extracted genetic material to identify the filtered pathogens. While operating the bioaerosol detector in accordance with the one or more first inputs, a change is identified in an operating condition for the bioaerosol detector. In response to identifying the change in the operating condition, the bioaerosol detector is operated in accordance with one or more second inputs. At least one input of the one or more second inputs is distinct from a respective input of the one or more first inputs.

In some embodiments, a bioaerosol detector includes a filter to filter pathogens from the air, an extraction kit to extract genetic material from the filtered pathogens, and a genetic sequencer and/or another component to analyze the extracted genetic material to identify the filtered pathogens. The bioaerosol detector also includes a controller with one or more processors and memory storing one or more programs for execution by the one or more processors. The one or more programs include instructions for performing the above method.

In some embodiments, a non-transitory computer-readable storage medium stores one or more programs for execution by one or more processors of a bioaerosol detector. The bioaerosol detector further includes a filter to filter pathogens from the air, an extraction kit to extract genetic material from the filtered pathogens, and a genetic sequencer and/or another component to analyze the extracted genetic material to identify the filtered pathogens. The one or more programs include instructions for performing the above method.

BRIEF DESCRIPTION OF THE DRAWINGS

For a better understanding of the various described implementations, reference should be made to the Detailed Description below, in conjunction with the following drawings.

FIG. 3 is a flowchart showing a method of bioaerosol detection in accordance with some embodiments.

FIG. 4 is a flowchart showing a method of performing bioaerosol detection based at least in part on a cost function, in accordance with some embodiments.

Like reference numerals refer to corresponding parts throughout the drawings and specification.

DETAILED DESCRIPTION

Reference will now be made in detail to various embodiments, examples of which are illustrated in the accompanying drawings. In the following detailed description, numerous specific details are set forth in order to provide a thorough understanding of the various described embodiments. However, it will be apparent to one of ordinary skill in the art that the various described embodiments may be practiced without these specific details. In other instances, well-known methods, procedures, components, circuits, and networks have not been described in detail so as not to unnecessarily obscure aspects of the embodiments.

Figure 1A:
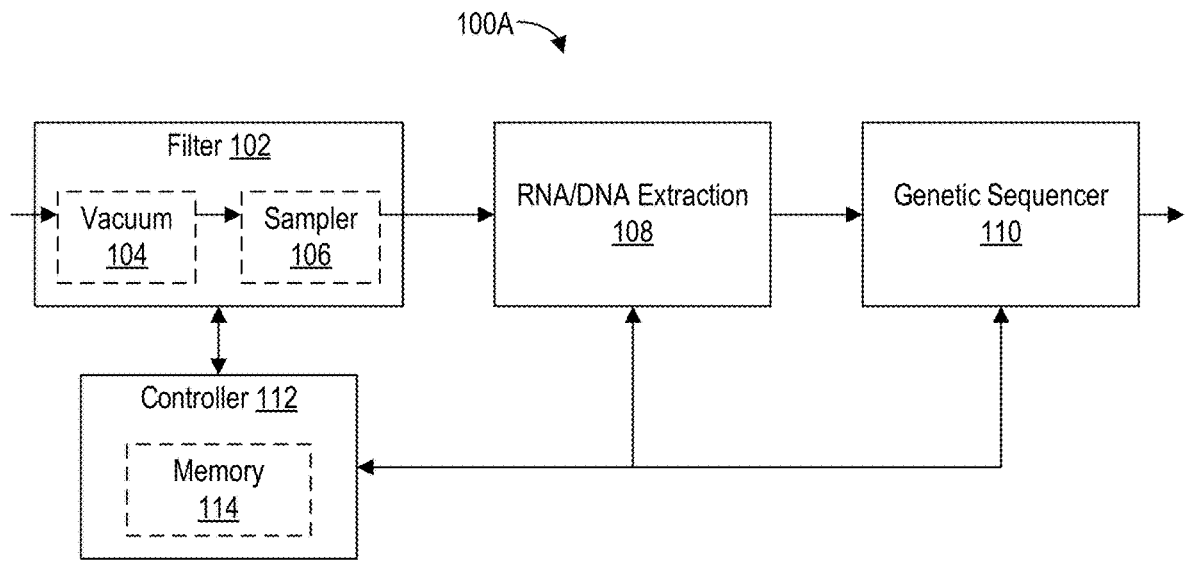
FIGS. 1A-1E are block diagrams of metagenomic bioaerosol detectors that can detect airborne pathogens, in accordance with some embodiments.

FIG. 1A is a block diagram of a metagenomic bioaerosol detector 100A that can detect airborne pathogens (e.g., viruses and/or bacteria), in accordance with some embodiments. The bioaerosol detector 100A includes a filter 102 to sample airborne pathogens, an RNA/DNA extraction kit 108 to extract genetic material from the pathogens collected by the filter 102, a genetic sequencer (i.e., gene sequencer) 110 (e.g., an Oxford Nanopore Minion sequencer or Illumina iSeq sequencer) to sequence the genetic material extracted by the extraction kit 108 and thereby identify a pathogen (e.g., identify a particular viral or bacterial species and/or strain), and a controller 112 to control operation of the filter 102, extraction kit 108, and/or genetic sequencer 110. The filter may include a vacuum 104 to take in air and a sampler 106 to sample pathogens (e.g., viruses and/or bacteria) in the air. In some embodiments, the sampler 106 has multiple porous stages, with each stage having a smaller porosity than the previous stage, such that viruses and/or bacteria may be collected at each stage. For example, the sampler 106 is an Andersen sampler. In some embodiments, the vacuum 104 has a capacity of approximately 10 liters per minute. In some embodiments, (e.g., for viruses, which have RNA but no DNA) the extraction kit 108 extracts RNA from pathogens collected by the filter 102 and converts the RNA to complementary DNA (cDNA), which is provided to the genetic sequencer 110 for sequencing. In other embodiments (e.g., for bacteria, which have DNA), the extraction kit 108 extracts DNA from pathogens collected by the filter 102 and provides the DNA to the genetic sequencer 110 for sequencing. The controller 112 provides control signals to the filter 102, extraction kit 108, and/or genetic sequencer 110. The control signals act as inputs that control operation of the bioaerosol detector 100A (e.g., that specify the operating mode for the bioaerosol detector 100A). These inputs are described further below for the method 300 (FIG. 3). The controller 112 may also receive signals from the filter 102, extraction kit 108, and/or genetic sequencer 110. These received signals may specify detection results (e.g., as determined by the genetic sequencer 110) and/or information regarding the operating status of respective components (e.g., of each component). The controller 112 may use these results and/or operating-status information to calculate and track statistics regarding operation of the bioaerosol detector 100A. The controller 112 may include a memory 114 (e.g., memory 810, FIG. 8) that stores instructions configured for execution by the controller 112 during operation of the bioaerosol detector 100A.

Figure 1B:
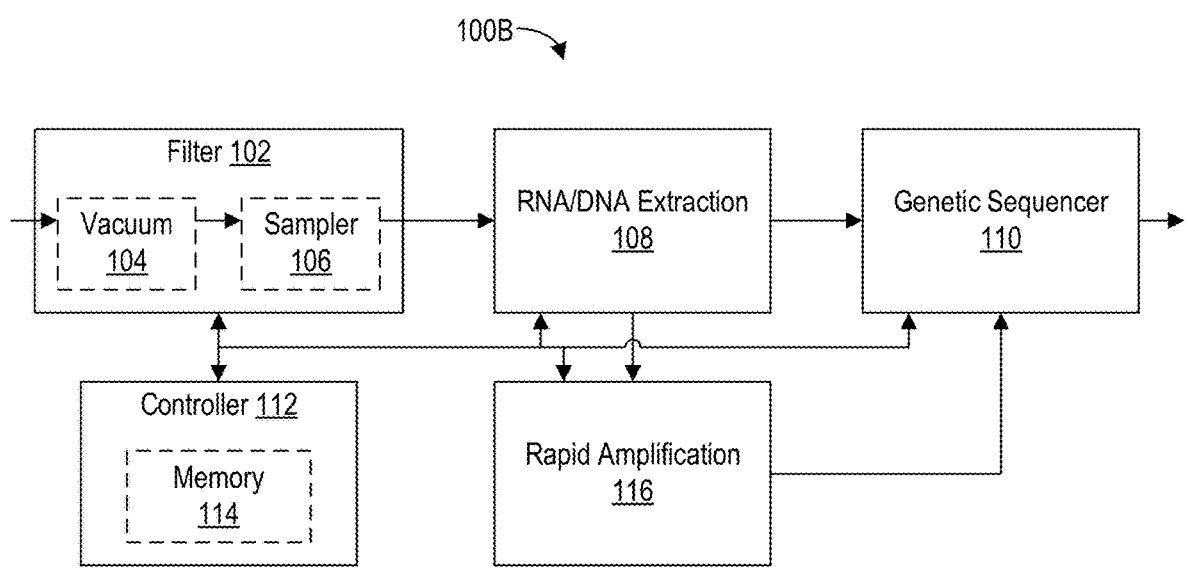

FIG. 1B is a block diagram of a metagenomic bioaerosol detector 100B that includes the filter 102, extraction kit 108, genetic sequencer 110, and controller 112 of the bioaerosol detector 100A, and also includes rapid amplification 116 for amplifying genetic material extracted by the extraction kit 108, in accordance with some embodiments. Amplified genetic material is provided to the genetic sequencer 110. Amplification increases the amount of genetic material available for sequencing but introduces a time delay. The rapid amplification 116 may perform targeted amplification (e.g., using the polymerase chain reaction (PCR)), such that only genetic material matching a target is amplified, and/or may perform untargeted, generic amplification of genetic material collected by the filter 102 regardless of viral or bacterial species or strain. The controller 112 may provide control signals to the rapid amplification 116, thereby providing inputs that control the amplification. For example, rapid amplification 116 may be enabled in a first operating mode for the bioaerosol detector 100B and disabled in a second operating mode for the bioaerosol detector 100B. The controller 112 may also receive signals from the rapid amplification 116 that provide information regarding the operating status of the rapid amplification 116.

Figure 1C:
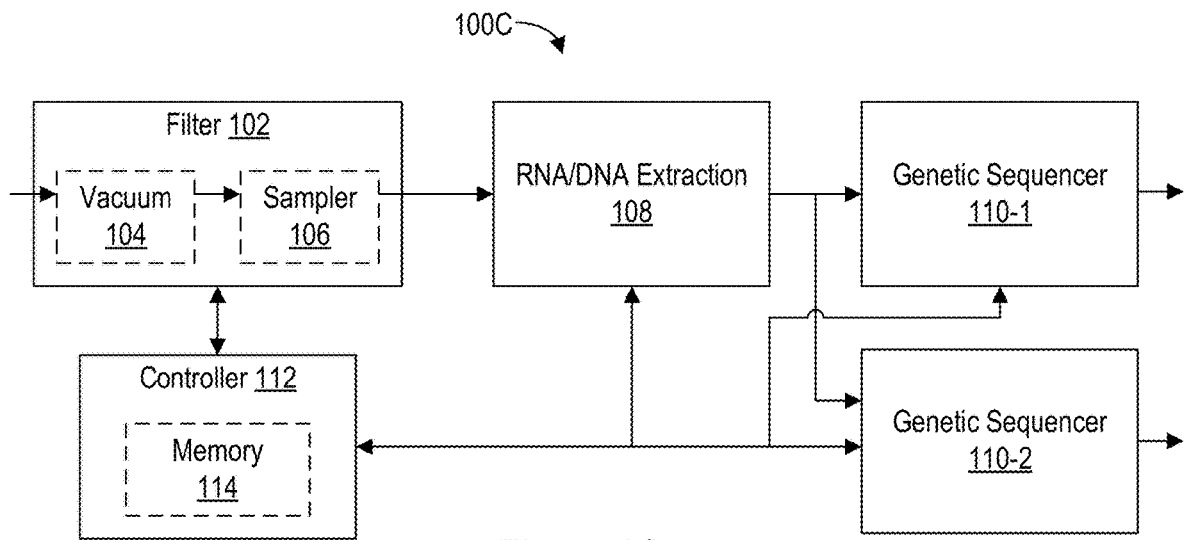
Figure 1D:
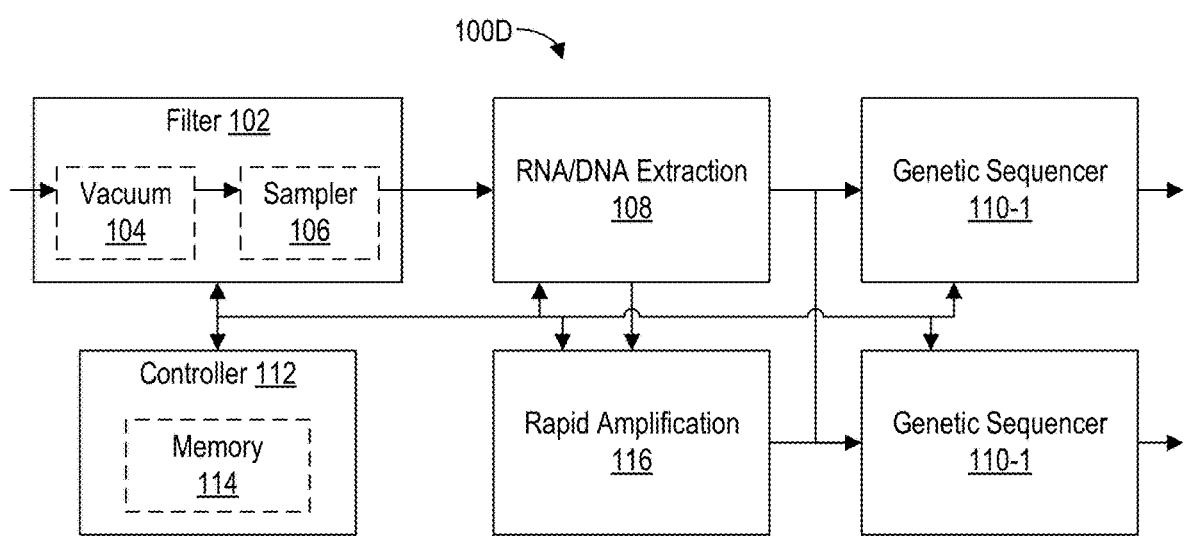

In some embodiments, a bioaerosol detector includes multiple genetic sequencers. FIG. 1C is a block diagram of a metagenomic bioaerosol detector 100C that includes the filter 102, extraction kit 108, and controller 112 of the bioaerosol detector 100A (FIG. 1A), and also includes two genetic sequencers 110-1 and 110-2, in accordance with some embodiments. FIG. 1D is a block diagram of a metagenomic bioaerosol detector 100D that includes the filter 102, extraction kit 108, rapid amplification 116, and controller 112 of the bioaerosol detector 100B (FIG. 1B), and also includes the two genetic sequencers 110-1 and 110-2. The controller 112 may provide control signals to both genetic sequencers 110-1 and 110-2, thereby providing inputs that control the genetic sequencers 110-1 and 110-2. For example, the first genetic sequencer 110-1 may be enabled in a first operating mode for the bioaerosol detector 100C or 100D and disabled in a second operating mode, while the second genetic sequencer 110-2 may be enabled in the second operating mode and disabled in the first operating mode. The controller 112 may also receive signals from both genetic sequencers 110-1 and 110-2 that specify detection results and/or information regarding the operating status of the genetic sequencers 110-1 and 110-2.

The genetic sequencers 110-1 and 110-2 may have different sequencing capabilities. For example, the first genetic sequencer 110-1 may perform sequencing with longer reads than the second genetic sequencer 110-2 (i.e., the first genetic sequencer 110-1 performs reads of a first length and the second genetic sequencer 110-2 performs reads of a second length that is shorter than the first length). In this example, the consumables for the short-read sequencing may be cheaper (per unit of sequencing, such as gigabases) than for the long-read sequencing, but the long-read sequencing may be faster.

Figure 1E:
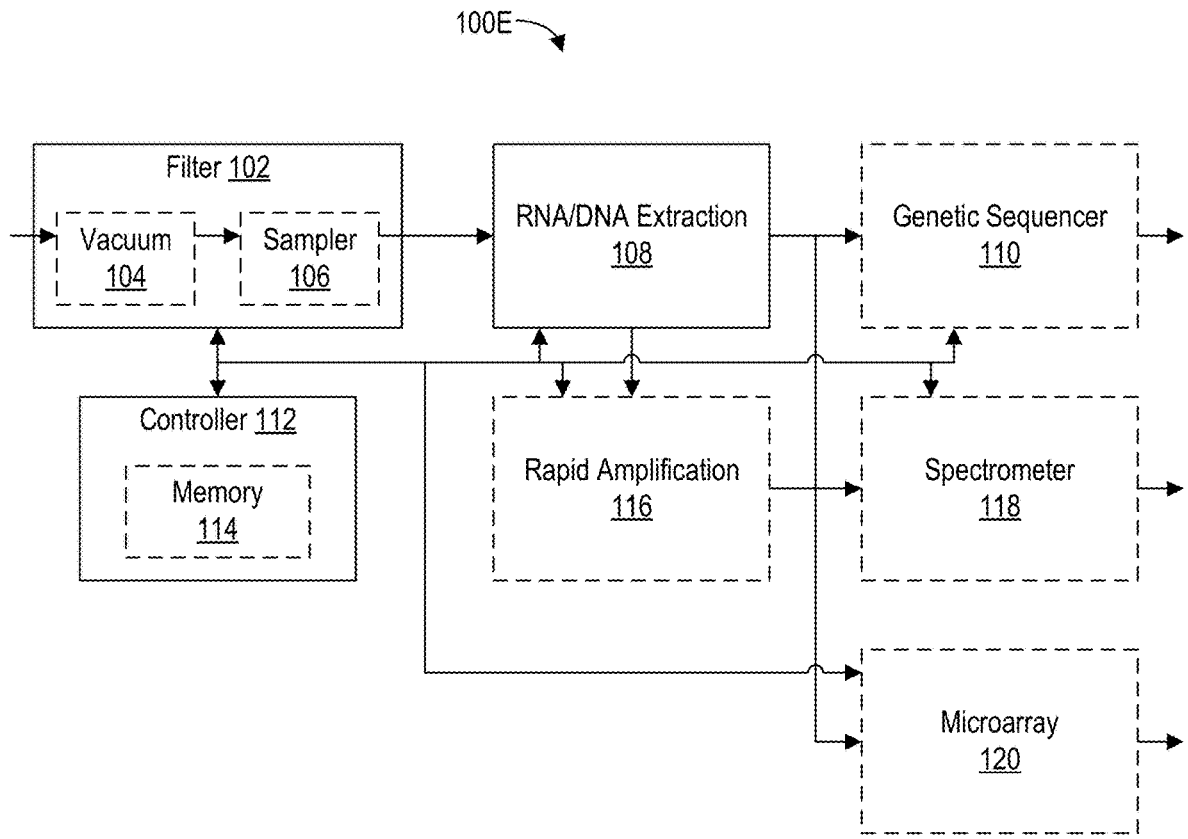

FIG. 1E is a block diagram of a metagenomic bioaerosol detector 100E that includes the filter 102, extraction kit 108, optional rapid amplification 116, and controller 112, in accordance with some embodiments. The bioaerosol detector 100E also includes a genetic sequencer 110 (or multiple genetic sequencers 110), one or more spectrometers 118 (e.g., including a mass spectrometer, charge-detection mass spectrometer, ion-mobility spectrometer, and/or differential-mobility spectrometer), microarray 120, and/or another component for identifying pathogens (e.g., viruses and/or bacteria) based on genetic material provided by the extraction kit 108 and/or rapid amplification 116. The spectrometer(s) 118, microarray 120, and/or other component may be used instead of or in addition to the genetic sequencer(s) 110 to identify pathogens. In some embodiments, each of the components used for identifying pathogens (i.e., genetic sequencer 110, spectrometer 118, and/or microarray 120) may operate alone in a respective operating mode for the bioaerosol detector 100E, and respective combinations of these components may operate together in respective operating modes for the bioaerosol detector 100E (e.g., with a distinct operating mode for each possible combination of components). For example, if the bioaerosol detector 100E includes a genetic sequencer 110 and spectrometer 118, the genetic sequencer 110 alone may be used to identify pathogens in a first mode, the spectrometer 118 alone may be used to identify pathogens in a second mode, and/or the genetic sequencer 110 and spectrometer 118 may be used together to identify pathogens in a third mode. The controller 112 selects the mode; control signals generated by the controller 112 specify the mode. In another example, if the bioaerosol detector 100E includes two spectrometers 118 (e.g., of different types), the first spectrometer 118 alone may be used to identify pathogens in a first mode, the second spectrometer 118 alone may be used to identify pathogens in a second mode, and/or the two spectrometers 118 may be used together to identify pathogens in a third mode. Again, the controller 112 selects the mode; control signals generated by the controller 112 specify the mode. If amplification is performed, pathogens may continue to be collected and have their genetic material extracted and analyzed (e.g., by the genetic sequencer 110, spectrometer 118, and/or microarray 120) while amplification is being performed, before amplification is completed. Performing amplification may take hours.

In some embodiments, instead of a single filter 102, a metagenomic bioaerosol detector 100A, 100B, 100C, 100D, or 100E includes multiple filters 102. The multiple filters 102 may be situated in different locations (e.g., in different rooms of a building). Genetic material is extracted from pathogens collected by the multiple filters 102 using either a single extraction kit 108 (e.g., in a centralized location in the building) or a plurality of respective extraction kits 108 (e.g., in the different rooms with the filters 102). A genetic sequencer 110 (e.g., in a centralized location in the building) sequences the extracted genetic material.

If the genetic material is extracted by a single extraction kit 108, then the filters 102 are repeatedly (e.g., periodically) transported from the locations at which they sample the air to the extraction kit 108 and back. If the genetic material is extracted by multiple extraction kits 108, then extracted genetic material is transported from the extraction kits 108 to the genetic sequencer 110 in repeating (e.g., periodic) manner. Changes to the sequencing rate result in corresponding changes to the rate of transportation of the filters 102 or extracted genetic material. If the sequencing rate increases, then the filters 102 are brought to the extraction kit 108 more frequently or the extracted genetic material from respective extraction kits 108 is brought to the genetic sequencer 110 more frequently, in accordance with some embodiments. If the sequencing rate decreases, then the filters 102 are brought to the extraction kit 108 less frequently or the extracted genetic material from respective extraction kits 108 is brought to the genetic sequencer 110 less frequently, in accordance with some embodiments.

The multiple filters 102 (and, in some embodiments, the multiple respective extraction kits 108) may be communicatively coupled with (e.g., controlled by) a single controller 112. Alternatively, multiple instances of a metagenomic bioaerosol detector 100A, 100B, 100C, 100D, or 100E may be situated in different locations (e.g., in different rooms of a building). Each instance of the metagenomic bioaerosol detector 100A, 100B, 100C, 100D, or 100E may have a distinct respective controller 112, or every instance of the metagenomic bioaerosol detector 100A, 100B, 100C, 100D, or 100E may share a single controller 112 (e.g., located in a centralized location).

Figure 2:
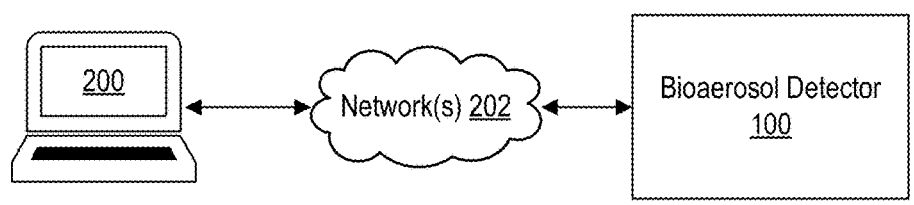
FIG. 2 is a block diagram of a system in which a bioaerosol detector is communicatively coupled to a remote computer system through one or more wired and/or wireless networks, in accordance with some embodiments.

FIG. 2 is a block diagram of a system in which a bioaerosol detector 100 (e.g., any of the bioaerosol detectors 100A-100E, FIGS. 1A-1E) is communicatively coupled to a remote computer system 200 through one or more wired and/or wireless networks 202, in accordance with some embodiments. The bioaerosol detector 100 (e.g., the controller 112) includes a network interface (e.g., network interface 803, FIG. 8) for communicating with the remote computer system 200 through one or more wired and/or wireless networks 202. The remote computer system 200 may receive data from the bioaerosol detector 100 (e.g., from the controller 112), including detection results identifying detected pathogens and information (e.g., statistics) regarding the operating status of the bioaerosol detector 100 (e.g., the current operating mode, previous operating modes, a record of control signals generated by the controller 112, levels of consumables used by the bioaerosol detector 100, values of a cost function for the bioaerosol detector 100, etc.). The remote computer system 200 may send instructions to the bioaerosol detector 100 (e.g., to the controller 112) requesting or specifying that the bioaerosol detector 100 operate in a particular operating mode. For example, the remote computer system 200 may send instructions specifying inputs to be provided by the controller 112 to other components of the bioaerosol detector 100. Alternatively, the controller 112 determines the inputs to be provided to other components of the bioaerosol detector 100 based on the instructions received from the remote computer system 200.

In response to identification of a pathogen, the bioaerosol detector 100 may raise an alarm. For example, the bioaerosol detector 100 may sound an alarm and/or display an alarm message locally, and/or transmit an alarm message to the remote computer system 200.

FIG. 3 is a flowchart showing a method 300 of bioaerosol detection in accordance with some embodiments. The method 300 may be performed by a bioaerosol detector 100 (e.g., any of the bioaerosol detectors 100A-100E, FIGS. 1A-1E). In some embodiments, the method 300 is performed under the control of the controller 112 (e.g., a bioaerosol-detection controller 800, FIG. 8).

In the method 300, a bioaerosol detector 100 is operated (302) in accordance with one or more first inputs (e.g., inputs generated by the controller 112) (e.g., is operated in a first operating mode). Operating the bioaerosol detector 100 includes filtering pathogens (e.g., viruses and/or bacteria) from the air, extracting genetic material from the filtered pathogens, and analyzing the extracted genetic material to identify the filtered pathogens. In some embodiments, analyzing the extracted genetic material includes (304) performing genetic sequencing of extracted genetic material to identify filtered pathogens. In some embodiments, analyzing the extracted genetic material includes (306) performing spectrometry (e.g., mass spectrometry, charge-detection mass spectrometry, ion-mobility spectrometry, and/or differential-mobility spectrometry) for extracted genetic material to identify filtered pathogens. In some embodiments, analyzing the extracted genetic material includes (308) using a microarray to analyze extracted genetic material to identify filtered pathogens. Examples of the one or more inputs include (310), without limitation, detection time, filtering rate, genetic-sequencing rate, false-positive detection rate, and/or false-negative detection rate.

A determination is made (312) as to whether a change in an operating condition for the bioaerosol detector 100 has occurred. For example, the controller 112 checks if a change in operating condition has occurred. The controller 112 may perform this check (i.e., make the determination 312) periodically and/or in response to data received from components of the bioaerosol detector 100. Examples of a change in the operating condition include, without limitation, a change in a background viral or bacterial concentration, a change in the concentration of a pathogen, a change in a ratio of the concentration of a pathogen to the background viral or bacterial concentration, a change in a desired detection time, a change in a desired sensitivity, a change in a desired degree of sequencing depth or redundancy, a change in a value of a cost function, a change in a false-positive or false-negative detection rate, and/or a time change.

The bioaerosol detector 100 operates in a cyclic manner. The filter 102 collects pathogens for a specified time period, after which they are provided to the extraction kit 108 (e.g., are washed off the sampler 106). The filter 102 then collects pathogens during a subsequent time period. The change may be a change detected during a particular time period or a change to one or more statistics calculated over multiple time periods.

If no change in the operating condition for the bioaerosol detector 100 is identified (312—No), the bioaerosol detector 100 continues to operate (302) in accordance with the one or more first inputs. If, however, a change in the operating condition for the bioaerosol detector 100 is identified (312—Yes), the bioaerosol detector 100 ceases to operate in accordance with the one or more first inputs and instead operates (314) in accordance with one or more second inputs (e.g., operates in a second operating mode). At least one input of the one or more second inputs (e.g., at least one of the inputs for step 310) is distinct from (e.g., has a different value than) a respective input of the one or more first inputs (e.g., all or a portion of the one or more second inputs are distinct from the one or more first inputs). Operating in accordance with the one or more second inputs may include continuing to filter pathogens (e.g., viruses and/or bacteria) from the air, extract genetic material from the filtered pathogens, and analyze the extracted genetic material to identify the filtered pathogens. In some embodiments, analyzing extracted genetic material when operating in accordance with the one or more second inputs includes performing genetic sequencing of extracted genetic material to identify filtered pathogens, performing spectrometry (e.g., mass spectrometry, charge-detection mass spectrometry, ion-mobility spectrometry, and/or differential-mobility spectrometry) for extracted genetic material to identify filtered pathogens, and/or using a microarray to analyze extracted genetic material to identify filtered pathogens.

The method 300 may be performed repeatedly. For example, a change in an operation condition for the bioaerosol detector 100 may be identified while the bioaerosol detector 100 is operating (314) in accordance with the one or more second inputs. In response, the bioaerosol detector 100 ceases to operate in accordance with the one or more second inputs and instead operates in accordance with one or more third inputs (e.g., operates in a third operating mode). At least one input of the one or more third inputs (e.g., at least one of the inputs for step 310) is distinct from (e.g., has a different value than) a respective input of the one or more second inputs.

In some embodiments, identifying (312—Yes) the change in the operating condition includes detecting a change in a concentration of a virus or bacteria in the air. In response, the rate of genetic sequencing as performed by a genetic sequencer 110 is changed: the genetic sequencing is performed at a different rate when operating the bioaerosol detector 100 in accordance with the one or more second inputs than when operating the bioaerosol detector 100 in accordance with the one or more first inputs. For example, a respective input of the one or more first inputs specifies a first rate for genetic sequencing, while a respective input of the one or more second inputs specifies a second rate for genetic sequencing distinct from the first rate.

In some embodiments, the viral or bacterial concentration for which the change is detected is a background viral or bacterial concentration. If the detected change is an increase in the background viral or bacterial concentration, then the rate of genetic sequencing is increased: the genetic sequencing is performed at an increased rate when operating the bioaerosol detector 100 in accordance with the one or more second inputs than when operating the bioaerosol detector 100 in accordance with the one or more first inputs. If the detected change is a decrease in the background viral or bacterial concentration, then the rate of genetic sequencing is decreased: the genetic sequencing is performed at a decreased rate when operating the bioaerosol detector 100 in accordance with the one or more second inputs than when operating the bioaerosol detector 100 in accordance with the one or more first inputs. The rate of genetic sequencing is increased when the background concentration increases to mitigate the effect of the decreased signal-to-noise ratio resulting from the increased background concentration. The rate of genetic sequencing is decreased when the background concentration decreases to reduce the operating cost in view of the increased signal-to-noise ratio that results from the decreased background concentration.

In other embodiments, the viral or bacterial concentration for which the change is detected is a concentration of a pathogen. If the detected change is a decrease in the concentration of the pathogen, then the rate of genetic sequencing is increased: the genetic sequencing is performed at an increased rate when operating the bioaerosol detector 100 in accordance with the one or more second inputs than when operating the bioaerosol detector 100 in accordance with the one or more first inputs. If the detected change is an increase in the concentration of the pathogen, then the rate of genetic sequencing is decreased: the genetic sequencing is performed at a decreased rate when operating the bioaerosol detector 100 in accordance with the one or more second inputs than when operating the bioaerosol detector 100 in accordance with the one or more first inputs. The rate of genetic sequencing is increased when the concentration of the pathogen decreases to offset the resulting decrease in sensitivity and detection time. The rate of genetic sequencing is decreased when the concentration of the pathogen increases to reduce the operating cost in view of the increased sensitivity and detection time that results from the increased concentration of the pathogen.

In some embodiments, identifying (312—Yes) the change in the operating condition includes detecting a viral species in the air (e.g., detecting a viral species that was not previously detected by the bioaerosol detector 100). In response, the rate of genetic sequencing is increased: the genetic sequencing is performed at an increased rate when operating the bioaerosol detector 100 in accordance with the one or more second inputs than when operating the bioaerosol detector 100 in accordance with the one or more first inputs. Increasing the rate of genetic sequencing in this context decreases the time taken to identify which strain of the viral species has been detected and/or the time taken to determine a concentration of the viral species in the air.

In some embodiments, identifying (312—Yes) the change in the operating condition includes detecting that a remaining amount of a consumable used to perform the genetic sequencing (e.g., used by the genetic sequencer) does not satisfy (e.g., is less than, or less than or equal to) a threshold. In response, the rate of genetic sequencing is decreased: the genetic sequencing is performed at a decreased rate when operating the bioaerosol detector 100 in accordance with the one or more second inputs than when operating the bioaerosol detector 100 in accordance with the one or more first inputs. Decreasing the rate of genetic sequencing conserves the consumable and thus allows the bioaerosol detector 100 to continue operating for a longer duration than would otherwise be possible in situations in which the consumable cannot be promptly resupplied. (The cost and rate of depletion of the consumable is proportional to the sequencing rate. Replacing the consumable may be difficult, for example if the bioaerosol detector 100 is located in a remote environment.) Similarly, in some embodiments, identifying (312—Yes) the change in the operating condition includes determining that a number (e.g., of total number) of sequenced pathogens satisfies a threshold. In response, the rate of genetic sequencing is decreased to conserve the consumable.

In some embodiments, the bioaerosol detector 100 includes a plurality of genetic sequencers (e.g., genetic sequencers 110-1 and 110-2, FIGS. 1C-1D). Genetic sequencing is performed using a first genetic sequencer of the plurality of genetic sequencers when operating the bioaerosol detector 100 in accordance with the one or more first inputs and is performed using a second genetic sequencer of the plurality of genetic sequencers when operating the bioaerosol detector 100 in accordance with the one or more second inputs. For example, a genetic sequencer with short reads is used in a first mode to save costs, while a genetic sequencer with long reads (i.e., longer than the short reads) is used in a second mode to decrease detection time.

In some embodiments, the filtering rate is changed in response to identifying (312—Yes) the change in the operating condition. Filtering is thus performed at a different rate when operating the bioaerosol detector 100 in accordance with the one or more second inputs than when operating the bioaerosol detector 100 in accordance with the one or more first inputs. The filtering rate may be changed by analogy to the genetic sequencing rate, using the same logic as described above for changes to the genetic sequencing rate.

In some embodiments, the bioaerosol detector 100 is capable of amplifying the extracted genetic material (e.g., includes rapid amplification 116, FIGS. 1B, 1D, and 1E). Amplifying the extracted genetic material (e.g., rapid amplification) is performed when operating the bioaerosol detector 100 in accordance with a first one of the one or more first or second inputs and not when operating the bioaerosol detector 100 in accordance with a second one of the one or more first or second inputs (e.g., is performed when operating the bioaerosol detector 100 in accordance with the one or more first inputs and not when operating the bioaerosol detector 100 in accordance with the one or more second inputs, or vice versa). For example, a respective input of the one or more first inputs may enable amplification and a respective input of the one or more second inputs may disable amplification, or vice versa. Amplification may be enabled and thus performed in response to detecting a decrease in a concentration of a virus or bacteria in the air (e.g., a decrease in background concentration or concentration of a pathogen), to provide sufficient starting material for genetic sequencing or to reduce detection time. Amplification may be disabled and thus not performed in response to detecting an increase in a concentration of a virus or bacteria in the air (e.g., an increase in background concentration or concentration of a pathogen), to reduce the operating cost or avoid the delay associated with amplification.

In some embodiments, the at least one input of the one or more second inputs that is distinct from the respective input of the one or more first inputs is selected to maintain at least one of a predefined maximum false-positive detection rate or a predefined maximum false-negative detection rate for detection of a mutation in a pathogen. Examples of changes identified in step 312 that result in this selection include, without limitation, environmental changes (e.g., to a pathogen or background concentration) or receiving an input (e.g., from a user or from the remote computer system 200). The change identified in step 312 may otherwise cause the predefined maximum false-positive detection rate and/or predefined maximum false-negative rate detection to exceed an acceptable limit.

In some embodiments, the controller 112 repeatedly calculates a cost function (e.g., the cost function of the method 400, FIG. 4, described below) indicative of a cost of operating the bioaerosol detector 100. Determining (312) whether a change in an operating condition for the bioaerosol detector 100 has occurred includes determining whether a value of the cost function has changed (e.g., whether the value has changed by an amount or magnitude that satisfies a threshold). Identifying (312—Yes) the change in the operating condition therefore may include detecting a change in the value of the cost function.

In some embodiments, the controller 112 generates a recommendation to install a new component in the bioaerosol detector 100 in response to identifying (312—Yes) the change in the operating condition (e.g., in response to detecting the change in the value of the cost function). For example, the controller 112 determines (e.g., based at least in part on the cost function) that the identified change will cause the bioaerosol detector 100 to fail to operate within specifications and that adding the new component will allow the bioaerosol detector 100 to operate within specifications despite the change. The bioaerosol detector 100 operates in accordance with the one or more second inputs after the new component has been installed. The cost function is updated to account for the new component. For example, terms are added to the cost function to account for the purchase cost of the new component, operating cost of the new component, and/or benefit of the new component.

In some embodiments, identifying (312—Yes) the change in the operating condition includes receiving an input (e.g., from a user or from the remote computer system 200) specifying the change. The at least one input of the one or more second inputs that is distinct from a respective input of the one or more first inputs is chosen based at least in part on the change and on an operating constraint for the bioaerosol detector ** time) versus cost (e.g., hourly cost) for a bioaerosol detector 100. (Identification time may also be referred to as detection time.) The model, which may correspond to the cost function, includes assumptions for pathogen density, air flow, average gene length, detection cost, fraction of pathogens detected, background to pathogen (e.g., total virus to target virus) ratio, and detected pathogen copies needed for identification. In one example, viral density $V=10^7$ per $m^3$, air flow $A=1.0$ $m^3$/hour, viral flow rate $F=V*A/60=166,667$ viruses per minute, average viral length $L=20$ kilobases, viral bases flow rate $B=L*F/10^6=3.33$ gigabases/minute, viral detection cost $C=\$30$/gigabase, fraction of viruses detected $X=1\%$, viral detection rate $R=V*A*X=10^5$/hour, viral detection rate $Rg=R*L/10^6=2$ gigabases/hour, detection cost $Ch=Rg*C=\$60$/hour, total virus to target virus ratio $H=100$, target viral density $D=V/H=10^5/m^3$, detected viral copies needed for identification $N=100$, and time to target viral identification $T=60*N/(D*A*X)=6$ minutes.

Figure 5A:
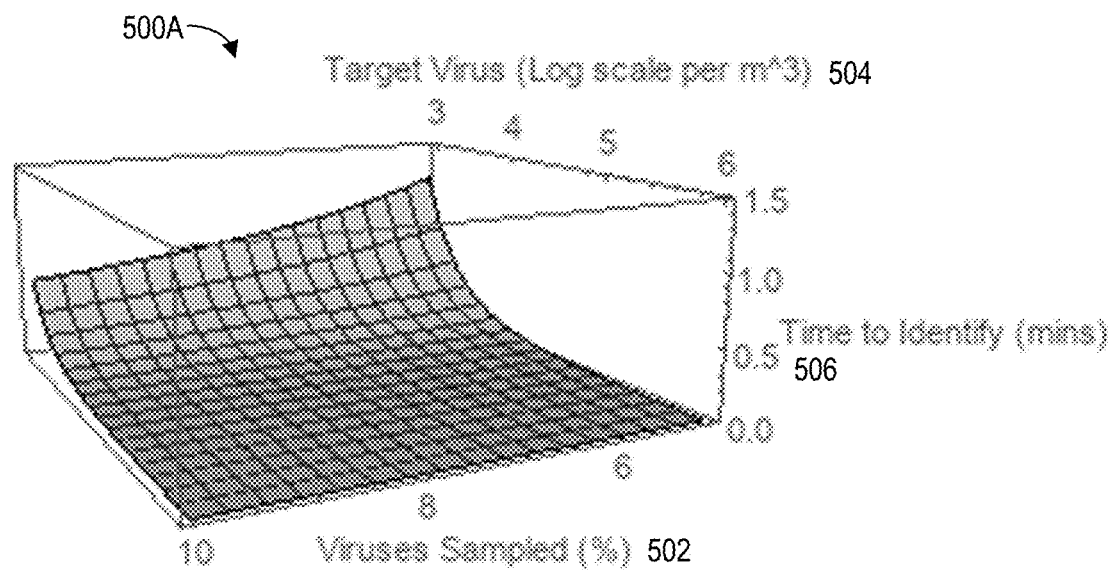
FIGS. 5A-5C are graphs showing estimated detection times for varying target-virus concentrations and fractions of viruses detected, in accordance with some embodiments.
Figure 5B:
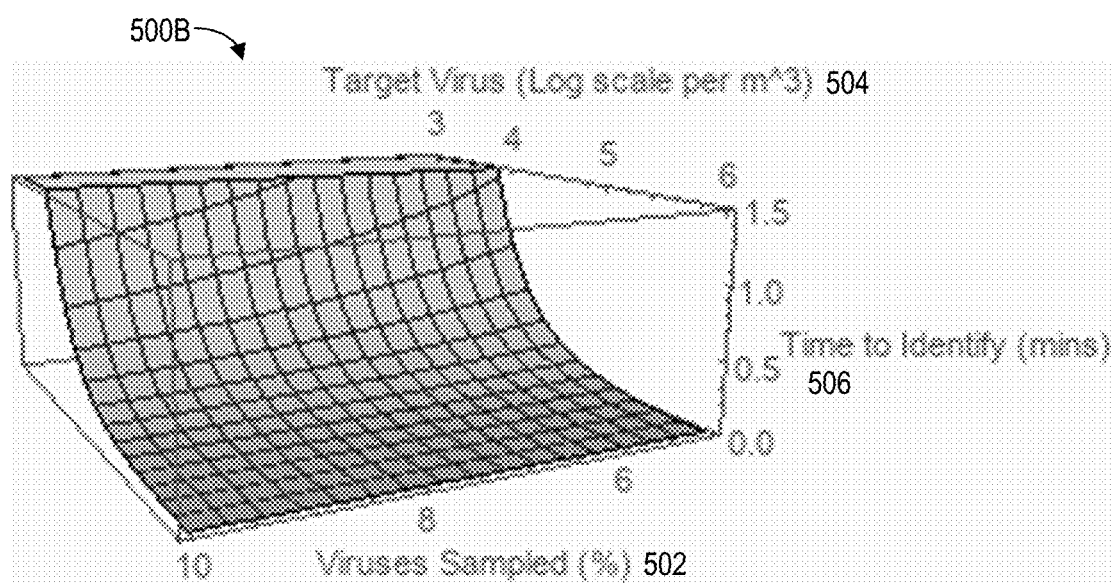
Figure 5C:
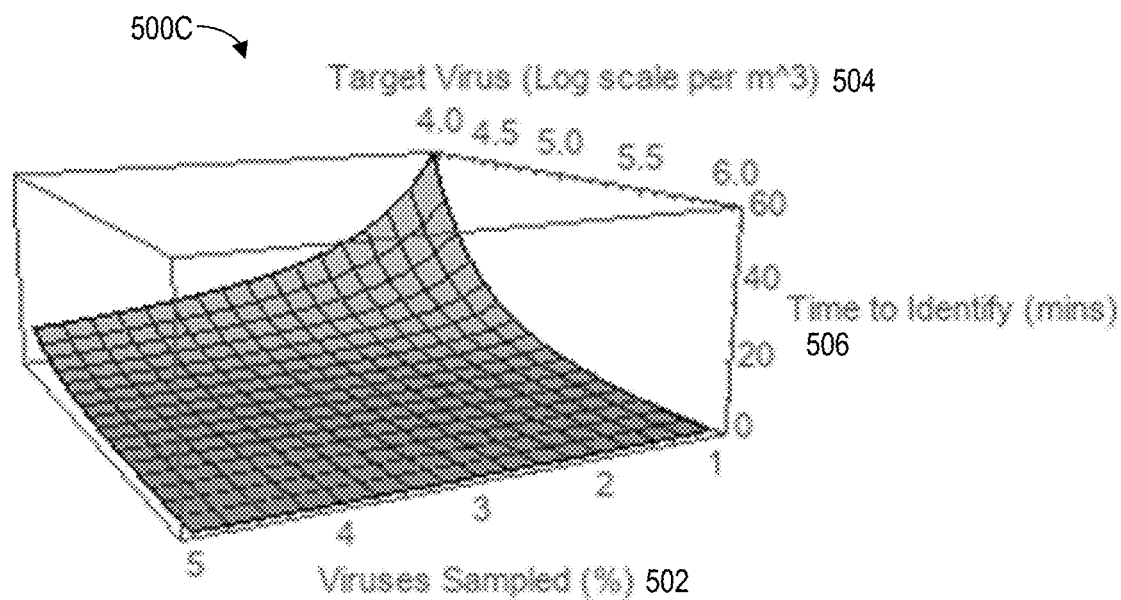
Figure 6:
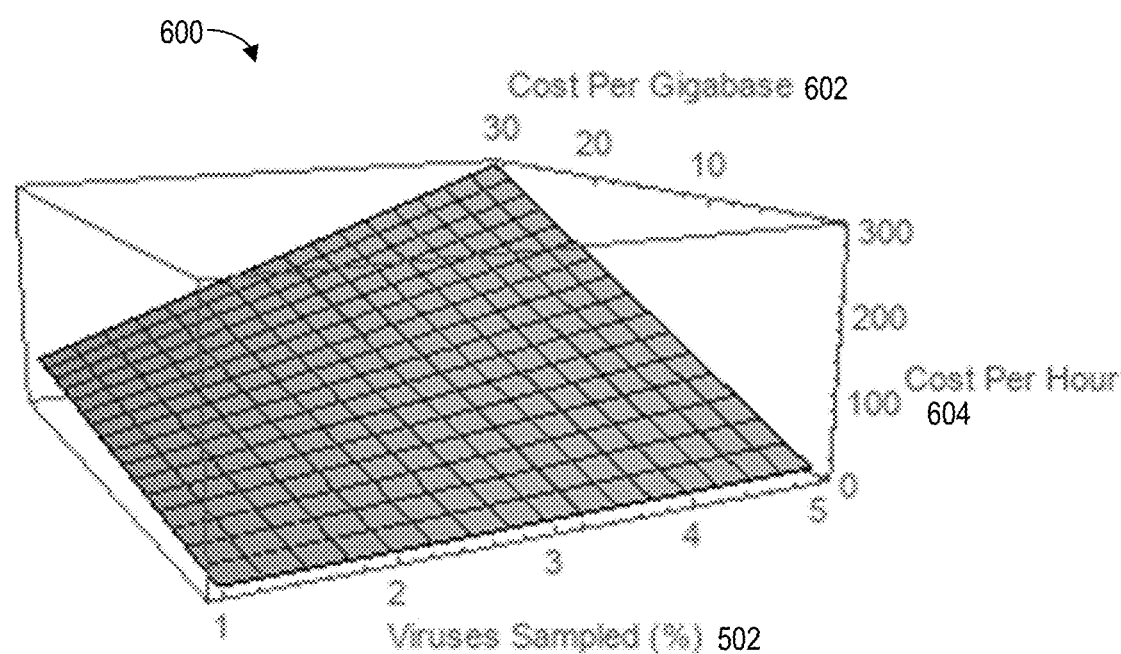
FIG. 6 is a graph showing costs for operating a bioaerosol detector, in accordance with some embodiments.

This model may be used to estimate the time and cost to detect different numbers of copies of a pathogen and to generate corresponding graphs. FIGS. 5A-5C are graphs 500A-500C showing estimated detection times 506 for varying target-virus concentrations 504 and fractions of viruses detected 502, in accordance with some embodiments. FIG. 5A assumes that identifying (e.g., sequencing) one copy of a virus is sufficient for detecting the virus, while FIG. 5B assumes that identifying (e.g., sequencing) 10 copies of a virus is sufficient for detecting the virus (i.e., detection is defined as having a threshold number of positive identifications equal to 10 in FIG. 5B). Detecting a particular viral strain (i.e., mutation) may require identifying higher numbers of copies of the viral species in which the strain is observed (i.e., may have a higher threshold number of positive identifications of the viral species). For example, 10-1000 viral copies may be needed to detect a mutation among non-mutated viruses. This threshold number of positive identifications may be calculated using the binomial distribution in accordance with the error rate of the genetic sequencer 110 and maximum tolerable false-positive rate. FIG. 5C shows estimated detection times 506 assuming that identifying (e.g., sequencing) 100 copies of a virus is sufficient for detecting the virus, while FIG. 6 is a graph 600 showing estimated costs per gigabase 602 and costs per hour 604 for varying fractions of viruses detected 502 for 100-copy detection. Comparing FIG. 5C to FIG. 6 shows tradeoffs between detection time and cost.

Figure 7:
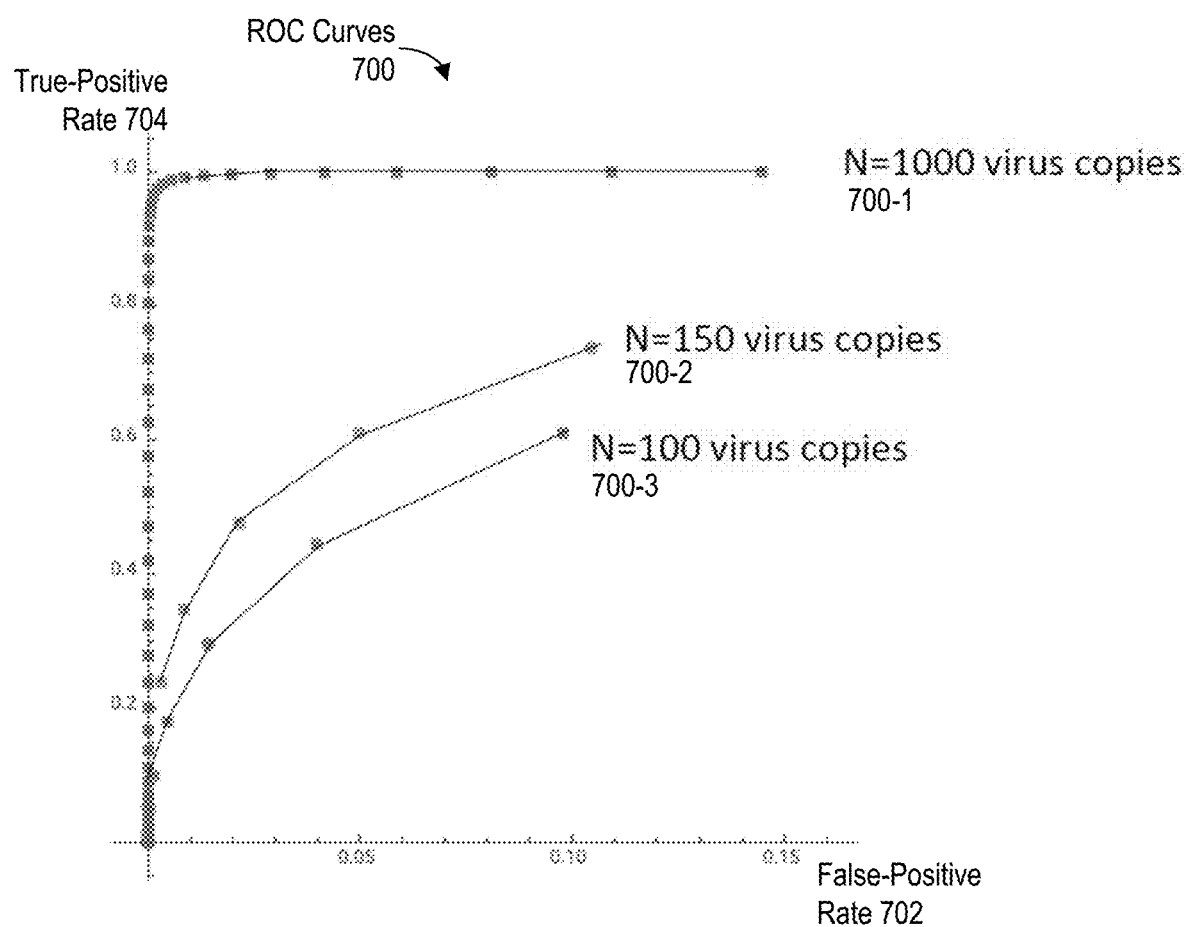
FIG. 7 is a graph showing examples of receiver operating characteristic (ROC) curves for varying numbers of viral copies used for detection, in accordance with some embodiments.

For true positives to exceed false positives, the error rate of the genetic sequencer 110 should not exceed the ratio of mutated to non-mutated pathogens (e.g., viruses or bacteria). The true-positive rate (i.e., true-positive detection rate) is the probability that mutations contribute to read of the mutation by the genetic sequencer 110. The true-positive rate depends on the allelic fraction of the mutation. The false-positive rate (i.e., false-positive detection rate) is the probability that sequencing errors contribute to read of the mutation by the genetic sequencer 110. The false-positive rate depends on the error rate of the genetic sequencer 110. FIG. 7 is a graph 700 showing examples of receiver operating characteristic (ROC) curves 700 for varying numbers of threshold viral copies used for detection, in accordance with some embodiments. The ROC curves 700 shows true-positive rates 704 versus false-positive rates 702 for the varying numbers of viral copies used for detection (i.e., varying threshold numbers of positive identifications). The numbers of viral copies used for detection include $N=1000$ for a first ROC curve 700-1, $N=150$ for a second ROC curve 700-2, and $N=100$ for a third ROC curve 700-3. The ROC curves 700 were generated assuming a mutant virus concentration of 25% of the target virus and a sequencer error rate of 17%.

Figure 8:
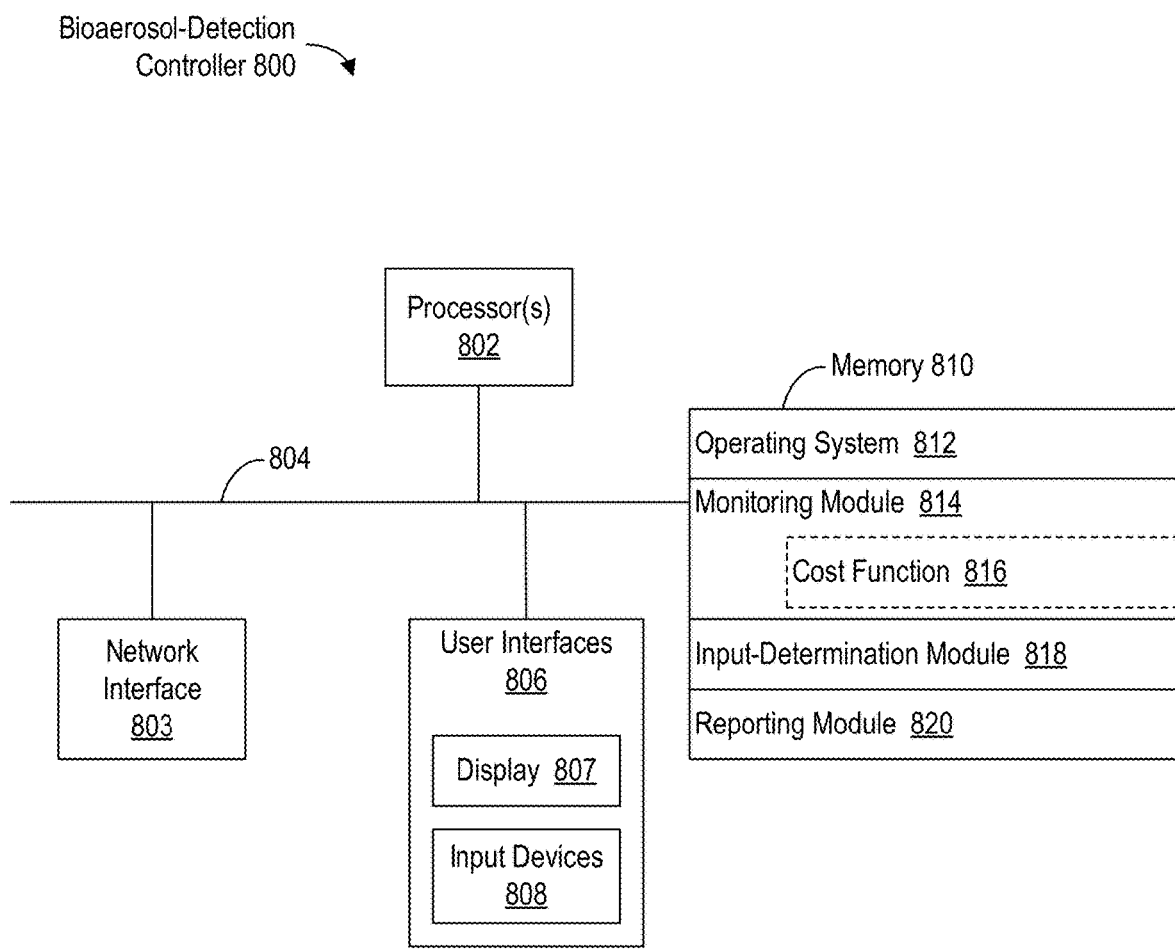
FIG. 8 is a block diagram of a bioaerosol-detection controller in accordance with some embodiments.

FIG. 8 is a block diagram of a bioaerosol-detection controller 800 in accordance with some embodiments. The bioaerosol-detection controller 800 is an example of a controller 112 (FIGS. 1A-1E). The bioaerosol-detection controller 800 includes one or more processors 802 (e.g., CPUs, microcontrollers, etc.), a network interface 803, optional user interfaces 806, memory 810, and one or more communication buses 804 interconnecting these components. The computer system may be communicatively coupled with the remote computer system 200 (FIG. 2) through the network interface 803 and one or more networks 202 (FIG. 2). In some embodiments, the bioaerosol-detection controller 800 is communicatively connected to other components of a bioaerosol detector 100 by the one or more communication buses 804. Alternatively, the bioaerosol-detection controller 800 is communicatively coupled to other components of the bioaerosol detector 100 through the network interface 803 and one or more networks.

The user interfaces 806 may include a display 807 and one or more input devices 808 (e.g., a keyboard, mouse, touch-sensitive surface of the display 807, etc.). The display 807 may report detection results (e.g., display an alarm message) and/or information regarding the operating status of the bioaerosol detector 100. In some embodiments, the user interfaces 806 include a speaker or other noise source for sounding an alarm.

Memory 810 includes volatile and/or non-volatile memory. Memory 810 (e.g., the non-volatile memory within memory 810) includes a non-transitory computer-readable storage medium. The memory 810 or a portion thereof (e.g., the non-volatile memory within memory 810) may be embedded within the processor(s) 802. Memory 810 optionally includes one or more storage devices remotely located from the processors 802 and/or a non-transitory computer-readable storage medium that is removably inserted into the bioaerosol-detection controller 800. In some embodiments, memory 810 (e.g., the non-transitory computer-readable storage medium of memory 810) stores the following modules and data, or a subset or superset thereof: an operating system 812 that includes procedures for handling various basic system services and for performing hardware-dependent tasks, a monitoring module 814 for monitoring operation of the bioaerosol detector 100 and identifying changes in operating conditions for the bioaerosol detector 100, an input-determination module 818 for determining inputs specifying how the bioaerosol detector 100 is to operate (e.g., the one or more first inputs and the one or more second inputs of the method 300, FIG. 3), and a reporting module 820 for generating reports to be displayed on the display 807 or transmitted to the remote computer system 200. The monitoring module 814 may include a cost function 816.

The memory 810 (e.g., the non-transitory computer-readable storage medium of the memory 810) thus includes instructions for performing all or a portion of the methods 300 (FIG. 3) and/or 400 (FIG. 4). Each of the modules stored in the memory 810 corresponds to a set of instructions for performing one or more functions described herein. Separate modules need not be implemented as separate software programs. The modules and various subsets of the modules may be combined or otherwise re-arranged. In some embodiments, the memory 810 stores a subset or superset of the modules and/or data structures identified above.

FIG. 8 is intended more as a functional description of the various features that may be present in a bioaerosol-detection controller than as a structural schematic. For example, the functionality of the bioaerosol-detection controller 800 may be split between multiple devices. A portion of the modules stored in the memory 810 may alternatively be stored in one or more computer systems communicatively coupled with the bioaerosol-detection controller 800 through one or more networks.

The foregoing description, for purpose of explanation, has been described with reference to specific embodiments. However, the illustrative discussions above are not intended to be exhaustive or to limit the scope of the claims to the precise forms disclosed. Many modifications and variations are possible in view of the above teachings. The embodiments were chosen in order to best explain the principles underlying the claims and their practical applications, to thereby enable others skilled in the art to best use the embodiments with various modifications as are suited to the particular uses contemplated.

What is claimed is:

1. A method of bioaerosol detection, comprising:
   operating a bioaerosol detector in accordance with one or more first inputs, the operating comprising:
   filtering pathogens from the air,
   extracting genetic material from the filtered pathogens, and
   analyzing the extracted genetic material to identify the filtered pathogens, comprising performing genetic sequencing;
   while operating the bioaerosol detector in accordance with the one or more first inputs, detecting a change in a concentration of a virus or bacteria in the air; and
   in response to detecting the change in the concentration of the virus or bacteria in the air, operating the bioaerosol detector in accordance with one or more second inputs, wherein:
   at least one input of the one or more second inputs is distinct from a respective input of the one or more first inputs, and
   the genetic sequencing is performed at a different rate when operating the bioaerosol detector in accordance with the one or more second inputs than when operating the bioaerosol detector in accordance with the one or more first inputs.

2. The method of claim 1, wherein:
   the concentration is a background viral or bacterial concentration;
   detecting the change in the concentration comprises detecting an increase in the background viral or bacterial concentration; and
   the different rate is an increased rate.

3. The method of claim 1, wherein:
   the concentration is a background viral or bacterial concentration;
   detecting the change in the concentration comprises detecting a decrease in the concentration; and
   the different rate is a decreased rate.

4. The method of claim 1, wherein:
   the concentration is a concentration of a pathogen;
   detecting the change in the concentration comprises detecting a decrease in the concentration of the pathogen; and
   the different rate is an increased rate.

5. The method of claim 1, wherein:
   the concentration is a concentration of a pathogen;
   detecting the change in the concentration comprises detecting an increase in the concentration of the pathogen; and
   the different rate is a decreased rate.

6. The method of claim 1, wherein:
   detecting the change in the concentration of the virus or bacteria in the air comprises detecting a viral species in the air; and
   the genetic sequencing is performed at an increased rate when operating the bioaerosol detector in accordance with the one or more second inputs than when operating the bioaerosol detector in accordance with the one or more first inputs.

7. The method of claim 1, wherein:
   the concentration is a pathogen concentration;
   detecting the change in the concentration of the virus or bacteria in the air comprises determining that a number of sequenced pathogens satisfies a threshold; and
   the genetic sequencing is performed at a decreased rate when operating the bioaerosol detector in accordance with the one or more second inputs than when operating the bioaerosol detector in accordance with the one or more first inputs.

8. The method of claim 1, wherein:
   the bioaerosol detector comprises a plurality of genetic sequencers;
   operating the bioaerosol detector in accordance with the one or more first inputs comprises performing the genetic sequencing using a first genetic sequencer of the plurality of genetic sequencers; and
   operating the bioaerosol detector in accordance with the one or more second inputs comprises performing the genetic sequencing using a second genetic sequencer of the plurality of genetic sequencers.

9. The method of claim 1, wherein:
   the filtering comprises sampling viruses or bacteria in the air; and
   the filtering is performed at a different rate when operating the bioaerosol detector in accordance with the one or more second inputs than when operating the bioaerosol detector in accordance with the one or more first inputs.

10. The method of claim 1, wherein:
    the bioaerosol detector is capable of amplifying the extracted genetic material;
    amplifying the extracted genetic material is performed when operating the bioaerosol detector in accordance with a first one of the one or more first or second inputs; and
    amplifying the extracted genetic material is not performed when operating the bioaerosol detector in accordance with a second one of the one or more first or second inputs.

11. The method of claim 10, wherein:
    detecting the change in the concentration of the virus or bacteria in the air comprises detecting a decrease in the concentration of the virus or bacteria in the air;
    amplifying the extracted genetic material is performed when operating the bioaerosol detector in accordance with the one or more second inputs; and
    amplifying the extracted genetic material is not performed when operating the bioaerosol detector in accordance with the one or more first inputs.

12. The method of claim 1, wherein the bioaerosol detector comprises a network interface to receive communications from a remote computer system, the method further comprising:
    while operating the bioaerosol detector in accordance with the one or more second inputs, receiving a communication from the remote computer system comprising an instruction to operate the bioaerosol detector using one or more third inputs; and in response to the instruction, operating the bioaerosol detector in accordance with the one or more third inputs,
wherein at least one input of the one or more third inputs is distinct from a respective input of the one or more second inputs.

13. The method of claim 1, wherein:
the bioaerosol detector comprises an Andersen sampler; and
the filtering comprises sampling pathogens in the air using the Andersen sampler.

14. The method of claim 1, wherein the bioaerosol detector comprises a plurality of filters, located in distinct respective locations, to filter the pathogens from the air.

15. The method of claim 1, wherein:
extracting the genetic material comprises:
    extracting RNA from the filtered pathogens, and
    converting the extracted RNA to complementary DNA (cDNA); and
performing the genetic sequencing comprises genetically sequencing the cDNA.

16. A bioaerosol detector, comprising:
a filter to filter pathogens from the air;
an extraction kit to extract genetic material from the filtered pathogens;
a genetic sequencer to analyze the extracted genetic material to identify the filtered pathogens; and
a controller comprising one or more processors and memory storing one or more programs for execution by the one or more processors, the one or more programs comprising instructions for:
    operating the bioaerosol detector in accordance with one or more first inputs;
    while operating the bioaerosol detector in accordance with the one or more first inputs, detecting a change in a concentration of a virus or bacteria in the air; and
    in response to detecting the change in the concentration of the virus or bacteria in the air, operating the bioaerosol detector in accordance with one or more second inputs, wherein at least one input of the one or more second inputs is distinct from a respective input of the one or more first inputs, and wherein the genetic sequencing is performed at a different rate when operating the bioaerosol detector in accordance with the one or more second inputs than when operating the bioaerosol detector in accordance with the one or more first inputs.

17. A non-transitory computer-readable storage medium storing one or more programs for execution by one or more processors of a bioaerosol detector, wherein the bioaerosol detector further comprises a filter to filter pathogens from the air, an extraction kit to extract genetic material from the filtered pathogens, and a genetic sequencer to analyze the extracted genetic material to identify the filtered pathogens; the one or more programs comprising instructions for:
    operating the bioaerosol detector in accordance with one or more first inputs;
    while operating the bioaerosol detector in accordance with the one or more first inputs, detecting a change in a concentration of a virus or bacteria in the air; and
    in response to detecting the change in the concentration of the virus or bacteria in the air, operating the bioaerosol detector in accordance with one or more second inputs, wherein:
        at least one input of the one or more second inputs is distinct from a respective input of the one or more first inputs, and
        the genetic sequencing is performed at a different rate when operating the bioaerosol detector in accordance with the one or more second inputs than when operating the bioaerosol detector in accordance with the one or more first inputs.

18. A method of bioaerosol detection, comprising:
operating a bioaerosol detector in accordance with one or more first inputs, the operating comprising:
    filtering pathogens from the air,
    extracting genetic material from the filtered pathogens, and
    analyzing the extracted genetic material to identify the filtered pathogens, comprising performing genetic sequencing;
while operating the bioaerosol detector in accordance with the one or more first inputs, detecting that a remaining amount of a consumable used in performing the genetic sequencing does not satisfy a threshold; and
in response to detecting that the remaining amount of the consumable does not satisfy the threshold, operating the bioaerosol detector in accordance with one or more second inputs, wherein:
    at least one input of the one or more second inputs is distinct from a respective input of the one or more first inputs, and
    the genetic sequencing is performed at a decreased rate when operating the bioaerosol detector in accordance with the one or more second inputs than when operating the bioaerosol detector in accordance with the one or more first inputs.

19. A method of bioaerosol detection, comprising:
operating a bioaerosol detector that comprises a plurality of genetic sequencers in accordance with one or more first inputs, the operating comprising:
    filtering pathogens from the air,
    extracting genetic material from the filtered pathogens, and
    analyzing the extracted genetic material to identify the filtered pathogens, comprising performing genetic sequencing using a first genetic sequencer of the plurality of genetic sequencers;
while operating the bioaerosol detector in accordance with the one or more first inputs, identifying a change in an operating condition for the bioaerosol detector; and
in response to identifying the change in the operating condition, operating the bioaerosol detector in accordance with one or more second inputs, comprising performing the genetic sequencing using a second genetic sequencer of the plurality of genetic sequencers, wherein at least one input of the one or more second inputs is distinct from a respective input of the one or more first inputs.

20. A method of bioaerosol detection, comprising:
operating a bioaerosol detector in accordance with one or more first inputs, the operating comprising:
    filtering pathogens from the air,
    extracting genetic material from the filtered pathogens, and
    analyzing the extracted genetic material to identify the filtered pathogens;
while operating the bioaerosol detector in accordance with the one or more first inputs, identifying a change in an operating condition for the bioaerosol detector; and in response to identifying the change in the operating condition, operating the bioaerosol detector in accordance with one or more second inputs, wherein:
    at least one input of the one or more second inputs is distinct from a respective input of the one or more first inputs, and
    the at least one input of the one or more second inputs is selected to maintain at least one of a predefined maximum false-positive detection rate or a predefined maximum false-negative detection rate for detection of a mutation in a pathogen.

21. A method of bioaerosol detection, comprising:
operating a bioaerosol detector in accordance with one or more first inputs, the operating comprising:
    filtering pathogens from the air,
    extracting genetic material from the filtered pathogens, and
    analyzing the extracted genetic material to identify the filtered pathogens;
repeatedly calculating a cost function indicative of a cost of operating the bioaerosol detector;
while operating the bioaerosol detector in accordance with the one or more first inputs, detecting a change in a value of the cost function; and
in response to detecting the change in the value of the cost function, operating the bioaerosol detector in accordance with one or more second inputs, wherein at least one input of the one or more second inputs is distinct from a respective input of the one or more first inputs.

22. The method of claim 21, further comprising, in response to detecting the change in the value of the cost function, generating a recommendation to install a new component in the bioaerosol detector, wherein:
    the bioaerosol detector operates in accordance with the one or more second inputs after the new component has been installed; and
    the cost function is updated to account for the new component.

23. A method of bioaerosol detection, comprising:
operating a bioaerosol detector in accordance with one or more first inputs, the operating comprising:
    filtering pathogens from the air,
    extracting genetic material from the filtered pathogens, and
    analyzing the extracted genetic material to identify the filtered pathogens, comprising performing genetic sequencing;
while operating the bioaerosol detector in accordance with the one or more first inputs, receiving an input specifying a change in detection time for a pathogen; and
in response to receiving the input specifying the change in the detection time:
    choosing at least one input of one or more second inputs based at least in part on the change and an operating constraint for the bioaerosol detector, the operating constraint being a genetic-sequencing budget or an available amount of a consumable used to perform the genetic sequencing, the at least one input being distinct from a respective input of the one or more first inputs, wherein the one or more second inputs include a different genetic sequencing rate than the one or more first inputs and at least one of a different false-positive detection rate or a different false-negative detection rate than the one or more first inputs; and
    operating the bioaerosol detector in accordance with the one or more second inputs.

* * * * *